(12) United States Patent
Campbell et al.

(10) Patent No.: US 8,252,576 B2
(45) Date of Patent: *Aug. 28, 2012

(54) USE OF PROKARYOTE VIRUSES TO REMEDIATE BIO-FOULING

(75) Inventors: Scott Campbell, The Woodlands, TX (US); Douglas Baldwin, College Station, TX (US); Mei Liu, College Station, TX (US); Neil S. Summer, College Station, TX (US)

(73) Assignee: Phage Biocontrol Research, LLC, College Station, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 13/177,315

(22) Filed: Jul. 6, 2011

(65) Prior Publication Data

US 2012/0040439 A1     Feb. 16, 2012

Related U.S. Application Data

(60) Provisional application No. 61/372,824, filed on Aug. 11, 2010.

(51) Int. Cl.
*C09K 8/52* (2006.01)
*C12N 7/00* (2006.01)
*C12N 1/00* (2006.01)
*C12N 1/20* (2006.01)

(52) U.S. Cl. .................. 435/235.1; 435/243; 435/252.1; 507/201

(58) Field of Classification Search .................. None
See application file for complete search history.

(56) References Cited

U.S. PATENT DOCUMENTS

| 4,778,653 | A | | 10/1988 | Kamimuta et al. |
| 4,999,286 | A | * | 3/1991 | Gawel et al. ................. 435/7.32 |
| 6,699,701 | B1 | | 3/2004 | Sulaknalidze et al. |
| 7,256,160 | B2 | * | 8/2007 | Crews .......................... 507/211 |
| 2009/0180992 | A1 | * | 7/2009 | Summer et al. .............. 424/93.6 |
| 2010/0243563 | A1 | | 9/2010 | Summer et al. |

FOREIGN PATENT DOCUMENTS

WO      WO 02/40642      *  5/2002

OTHER PUBLICATIONS

Zuo et al. (Applied Microbiology and Biotechnology. 2004; 64: 275-283).*
Zuo, Green, Hsu, Mansfield and Wood; Inhibiting mild steel corrosion from sulfate-reducing bacteria using antimicrobial-producing biofilms in Three-Mile-Island process water. Journal of Applied Microbiology and Biotechnology. 2004; 64: 275-283.
Sakaguchi, et al (Control of Microbiofouling Using Bacteriophage 2. Detection of Phages and Fundamental Study of Their Lytic Effect on Fouling Bacteria (Abstract Only), De 1989.
Lee, et al (Molecular analysis of a mixed-species biofilm on carbon steel. Abstracts of the General Meeting of the Americam Society for Microbiology, 2003; vol. 103:Q-156).
Zacheus et al, Soft Deposits, The Key Site for Microbial Groth in Drinking Water Distribution Networks; Wat. Res. Vi ol. 35, No. 7, pp. 1757-1765,2001.

* cited by examiner

*Primary Examiner* — Shanon A Foley
(74) *Attorney, Agent, or Firm* — Douglas Baldwin

(57) ABSTRACT

This invention provides a process for control in oil and gas wells and related facilities of prokaryote caused souring, fouling and corrosion by reduction of problematic prokaryotes with naturally occurring lysing organisms, particularly sulfate-reducing prokaryotes by proliferating suitable virulent lysing organisms under conditions in which problematic prokaryotes thrive, including in a gas production wellbore. The process provides in situ proliferation of virulent lysing organism in a wellbore by providing both virulent lysing organisms and their host prokaryotes to selectively grow an effective control amount and concentrations of lysing organisms in a well formation.

12 Claims, 3 Drawing Sheets

USE OF PROKARYOTE VIRUSES TO REMEDIATE BIO-FOULING

RELATION TO OTHER APPLICATIONS

The present application claims benefit under 35 U.S.C. §119(e) of U.S. Provisional Patent Application No. 61/372,824, filed Aug. 11, 2010, entitled "Process for Continuous Production of Bacteriophage" the disclosure of which is hereby incorporated by reference in its entirety for all purposes.

BACKGROUND

1. Field of the Invention

This invention relates to control of biofouling in oil and gas wells and facilities caused by sulfate reducing prokaryotes. More specifically, it relates to control of prokaryote caused souring, fouling and corrosion by reduction of problematic prokaryotes with naturally occurring lysing organisms, particularly sulfate-reducing prokaryotes by proliferating suitable virulent lysing organisms under conditions in which problematic prokaryotes thrive, including in a gas production wellbore.

2. Background

Microbial fouling is a serious problem in the oil and gas industry. Microbial-evolved hydrogen sulfide sours oil and gas reservoirs, elevates risk and devalues the product. Microbial produced iron sulfide production creates black powder accumulation, causing piping, and pipeline blockages. Microbial-influenced corrosion attacks the whole oil and gas system from fracture tank to refinery. Microbes also degrade fracture fluid additives.

These problems are especially acute in shale gas operations. Gas-containing shale geological formations such as the Barnett Shale in Texas and the Marcellus Shale in the eastern US require use of large-volume hydraulic fracturing technologies.

In a typical hydrofracture operation, 11-19 million liters (2.9 to 5 million gallons) of water is collected in large purpose-dug ponds ("frac ponds") from a variety of sources; aquifers, chlorinated city water, pond, river and lake water. Each of these water sources have some level of indigenous prokaryote microorganism (bacterial and archaeal) populations that will maintain activity in active viable numbers, and will accumulate during the ponds' period of open exposure. Further, water recovered from previous hydro-fracture operations, "flow-back" or "produced" water, is typically re-used by mixing with this frac pond water. If the water is not treated correctly, recycling can lead to "black water", scaling, souring, and MIC (microbiologically influenced corrosion).

Sulfate reducing prokaryotes endemic to or introduced into the formation will encounter favorable growth conditions during the hydrofracture operation. Upon completion some gas wells are "shut in" while surface processing equipment and flow-lines are installed, leaving time for microorganisms to colonize. Ultimately, viable microorganisms within biofilms can produce the sulfide necessary to sour a sweet gas reservoir, and contaminate flow lines, water tanks, and disposal facilities. Aside from the extreme costs of reservoir souring, many tight shale gas productions in the US are solely dependent on the ability to treat and dispose of the flowback (produced) water. Therefore, the water either utilized or produced, is often key to the commercial viability of the gas developments.

To counter bacterial fouling, reservoir souring, and to "clean" water for disposal broad spectrum chemical biocides are used. For a biocide to work, it must diffuse and kill at rates faster than the growth rate of bacteria. If biocides are unable to do so then prokaryote microorganisms grow within the pores of the reservoir formation, in biofilms which bud off inoculums to contaminate downstream through laterals, tubulars, and mobile processing equipment. With the porosity of the formation rock at nanodarcy size, developing biofilm can easily choke off the well, ultimately affecting the conductivity and thus productivity of the gas well.

These broad spectrum chemicals cost the oil industry over $200 million annually, while the cost of "corrosion" to oil upstream production and gathering systems, flowlines, and liquid transmission pipelines is estimated at $7 billion annually in the US alone. Tetrakis (hydromethyl) phosphonium sulfate (THPS) and hypochlorite bleach are the most commonly used antimicrobials in the Barnett shale operations area and cost approximately $50,000 each hydrofracing operation. Customary biocides include glutaraldehyde, glutaraldehyde/quaternary ammonium compound blends, isothiazolin, tetrakis(hydromethyl)phosphonium sulfate (THPS), 2,2-dibromo-3-nitrilopropionamide, and bronopol. However these biocides often have major health risks to humans and all animals in the food chain.

It is uncertain whether the currently used biocides are even effective against sulfate reducing archaea. Further compounding the issue of toxicity, many of the biocides within hydrofracing systems have proven to be less than effective as numerous turnkey gas wells have become sour, and many disposal wells and horizons are being quickly plugged. Flow back water recycling is being reduced, and water shortages and fouling issues are threatening to curtail exploration and production in tight gas shale areas.

The scale of the problem is enormous. The Barnett Shale extends over 5,000 square miles in north central Texas. A total of 6,519 gas wells with a further 4,051 permitted locations existed as of Aug. 15, 2007. Wells are being drilled within populated areas such as the Dallas-Fort Worth city limits where it is vital to minimize risk and environmental impact.

EPA registered biocides cannot be introduced into open ponds as they will permeate into the groundwater, killing aquatic organisms and ultimately be consumed by terrestrial animals, and possibly humans. Since biocides may remain in residual flowback and produced water, this water constitutes a waste handling and disposal issue. Overall, biocide usage in the petroleum industry is facing growing regulatory resistance due to its negative impact on the environment and associated health risks.

Another problem with biocide use is in assessing their effectiveness. In typical biocide assessment practices, samples of hydrofracture water are diluted and cultured in specialized growth medium under various conditions, with and without biocide, for various lengths of time and then compared for bacterial cell density, resulting in more than 40 test cultures each time. There are seasonal variations in bacteria, requiring different growth and test conditions, to which the bacteria may respond differentially. The results take days and thus cannot be used for optimization of biocide application. The typical field solution to this uncertainty is to apply massively excessive concentrations of sodium hypochlorite (*Use of Microbiocides in Barnett Shale Gas Well Fracturing Fluids to Control Bacteria Related Problems*; J. K. Fisher, K. Johnson, K. French and R. Oden, Paper 08658, NACE, International; 2008 Corrosion Conference and Expo).

Moreover, these field tests vastly underestimate the variety, type and amount of sulfate reducing microorganism that are actually present in the water and that are present in the wellbore (Larsen, Soresen, Hojris and Shovas; *Significance of*

*Troublesome Sulfate-Reducing Prokaryotes (SRP) in Oil Field Systems*; Paper 09389, NACE Corrosion 2009 Conference and Expo).

"Sulfide generation by sulfate-reducing prokaryotes (SRP) is the major cause of reservoir souring ad microbiologically influenced corrosion (MIC). The monitoring of SRP in oil fields is typically carried out by cultivation based methods. It is widely accepted that the cultivation approach grossly underestimates population sizes by several orders of magnitude due to the majority of SRP in oil field samples being not readily viable in selective culture media."

"Only a small fraction (usually less than 1%) of the microorganisms in a sample will grow in enrichment media in the laboratory. Nevertheless, monitoring of microbiological sulfide production in relation to souring and MIC in the oil industry still rely largely on cultivation-based techniques such as the most probable number (MPN) technique, potentially resulting in severe misinterpretation of the actual system condition."

As an example, it has become clear that sulfide is not only produced by sulfate-reducing bacteria (SRB), but also by a group of Archaea (sulfate-reducing Archaea, SRA), methanogens and even fermentative microorganisms in the oil field system."

In addition to oil and gas wells that are hydrofractured, other reservoirs are "flooded" with water to enhance oil recovery. In flooding, water is pumped into an injection well to push the oil and/or gas through a formation into "recovery" well(s) in the same field. Since water is injected into the reservoir and it is also contaminated with the same type organisms as the water for hydrofracturing, the same problems of souring, fouling and corrosion occur.

A better control strategy would be: inexpensive to manufacture, environmentally benign, able to evolve with the microorganisms and thus prevent resistance, be targeted towards those microorganisms that constitute the threat and be able to penetrate and destroy biofilms. Such a control strategy would also, optionally, be able to sense and adjust to the different concentrations of microorganisms encountered, even within the well. The present invention is just such a strategy based on bacteriophage or archaeal viruses, the natural predators of prokaryotes (bacteria and archae). Bacteriophage are used as an example to illustrate this invention.

SUMMARY OF THE INVENTION

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention is a safe natural environmentally sound means of controlling microbial biofouling—contamination, corrosion, fouling and souring—in oil and gas wells that result from prokaryote contaminated water in an oil or gas well. More specifically, in one embodiment, the invention is a method of remediating sulfate-reducing prokaryotes (SRP) in oil and gas geological formations by introducing into a wellbore in a geological formation a combination of sulfate-reducing prokaryotes (SRP) and lysing organisms (LO) virulent for said sulfate-reducing prokaryotes (SRP) in sufficient amount and concentration to cause the lysing organisms to replicate by lysing matching host sulfate-reducing prokaryotes (SRP).

In another embodiment the invention is a composition comprising prokaryotes recovered from "produced water".

In another embodiment the invention is a composition comprising prokaryote lysing organism recovered from "produced water".

Other more specific embodiments are disclosed in the Detailed Description. The technology of this invention will improve operational efficiencies and prolong the operational life of marginal wells that would ordinarily have been withdrawn from service. It will also decrease the capital costs of creating new wells by maintaining sweet gas production, mitigating the need for sour service piping and hydrogen sulfide removal apparatus. The ability to recycle flowback water will decrease the cost of, and environmental impact of hydrofracture operations, and thus new wells. An ancillary benefit will be the improvement of results from hydrofracture operations.

DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION

The present invention is a process for controlling the problem sulfate reducing prokaryotes that utilizes lysing organisms virulent for such prokaryotes, instead of synthetic biocides.

Bacteriophages, or phages, that are capable of lysing bacteria (a prokaryote) are the ubiquitous and natural viruses which infect, are reproduced within, and kill bacteria. Phage infection is initiated when the tail proteins recognize and adsorb to specific cell surface features of the target bacterial host. This triggers the injection of the phage DNA into the bacterial cytoplasm. The genes in that DNA are expressed by the bacterium's own protein synthesis apparatus, resulting in the synthesis and assembly of approximately 20 to 100 progeny phage particles over the course of minutes to several hours. After, typically, 15 to 60 minutes, the cell is disrupted ("lysis") as a result of phage-encoded lytic enzymes, liberating of progeny phage that can adsorb to new bacterial hosts and repeat the process. In this manner, bacteriophage replicate themselves according to the bacteria present. Random environmental samples indicate the presence of 10-100 phage for every bacterial cell, indicating $10^{30}$-$10^{31}$ phage in the biosphere!

Phages do not infect plants or animals and are therefore safe to produce, store, handle and apply, and some have been "Generally Recognized as Safe" for use in human food. Because bacteriophage reproduce along with the microorganisms that they infect, they will spread once down-well to other bacteria of the same species that otherwise would not be affected.

Other prokaryotes, archaea, similarly exist in nature and behave in a similar manner.

As used herein sulfate reducing prokaryotes (SRP) mean both sulfate reducing bacteria and archaea. Prokaryote lysing organisms (LO) mean organisms capable of destroying a prokaryote by infecting it, replicating itself inside the prokaryote and bursting the infected prokaryote, and include bacteriophage for bacteria and archaeal viruses for archaea. This invention is primarily directed to use of bacteriophage and archaeal viruses.

As used herein the following definitions apply: A prokaryote lysing organism cocktail includes multiple, receptor independent lysing organisms for each target prokaryote host. This is different from a prokaryote lysing organism panel, which is a collection of lysing organisms chosen to cover as wide a host range as possible. For the purposes of this invention the treatment solution will generally consist of a panel of cocktails, that is, there will generally be at least two virulent organisms for each target prokaryote and lysing organism cocktails for each of several target SRP. Since some SRP lysing organisms are known to be polyvalent—effective against more than one strain of SRP—there may be no need for a separate cocktail for every strain of target SRP. This panel of cocktails is designated herein as phage "lysing organism multi-panel".

The Process

Figure 1:
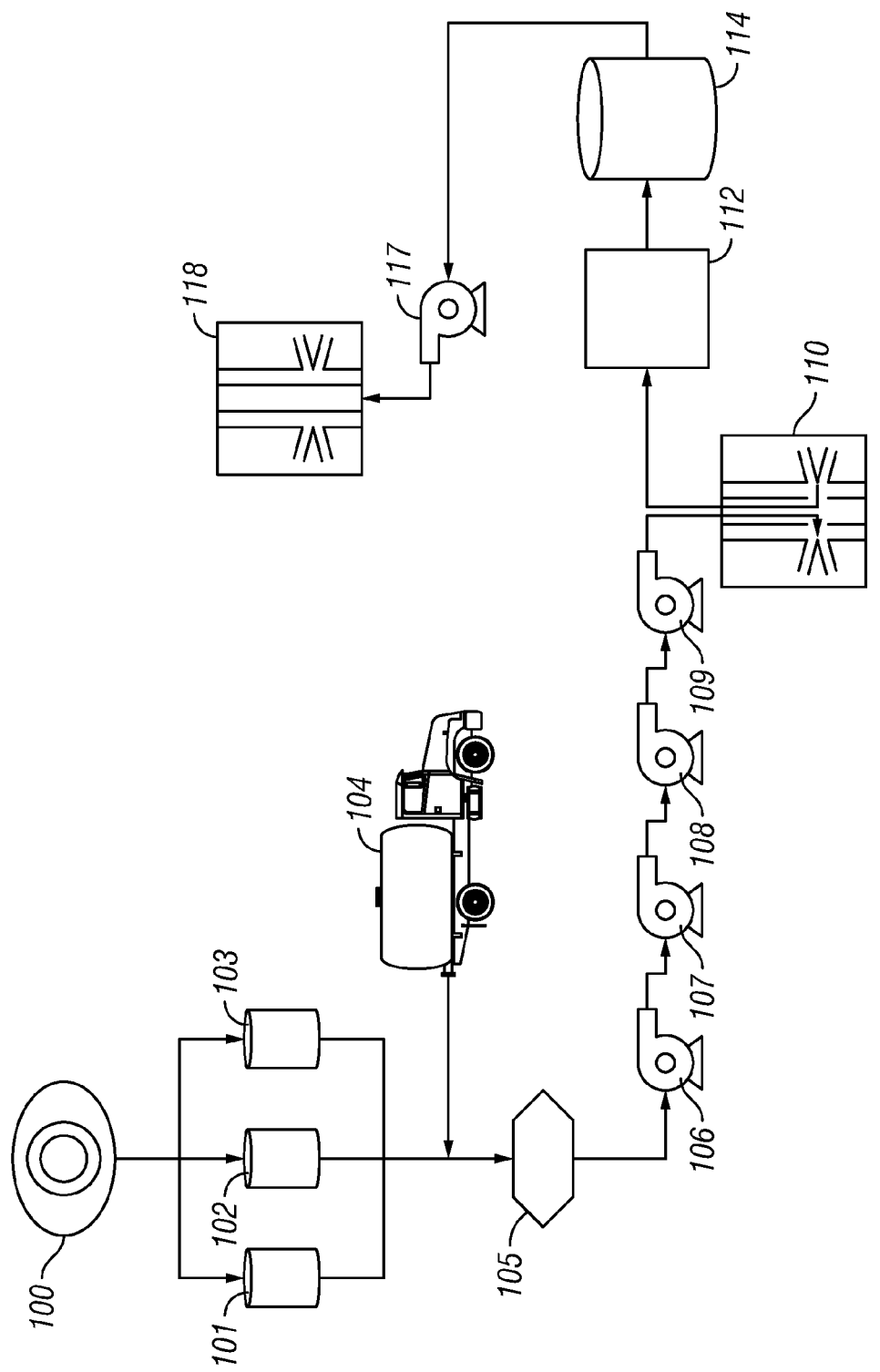
FIG. 1 is a. diagrammatic representation of the process of and equipment for hydrofracturing a gas well.

The process of the invention is illustrated by reference to the Figures. FIG. 1 illustrates a typical flow scheme for a hydrofracturing ("frac" or "fracing") operation (as, for example, in a Barnett Shale or Marcellus Shale gas wells). Water from a lined storage pit, 100, is pumped into one of several 500 bbl temporary storage tanks, 101, 102 and 103, or the tanks filled directly from other water sources. Water in the storage pit may be tanked in, produced from water well(s), river water, natural run-off water or any other convenient source. For reference, a half acre pit of 6 ft average depth contains 488,779 gallons. Many of the water sources will be heavily contaminated with prokaryotes, including SRP. Since the pit generally is open it will have additional air-borne and run-off contamination with numerous and varied microbiological strains.

Water from the temporary storage tanks is mixed (in the blender 105) with chemical additives and proppants to hold the fractures open (usually sand or ceramic beads), biocides from tank (usually a tank truck, 104) and other chemicals. Water and additives are mixed in a blender, 105, and picked up by high pressure pump(s), 106-109, for high pressure injection into a wellbore 110. The well bore is sealed up-well of the to-be-fractured area by packer(s) (252 in FIG. 2) to contain the pressure in the wellbore during "fracing". Water pumping rates range from about 10 bbl/minute to as much as 200 bbls/minute (420-8,400 gal. per min.). Rates of 70-80 bbls/minute are typical in Barnett Shale wells. The "frac" water may be injected in one or more stages or to individual segments of the well bore. For example, the segment of the deepest portion of the well may be sealed and fractured then filled with sand (or other sealant) and the tools pulled back to seal and fracture a second segment and so on. For the purposes of this invention each of these segments may be considered a separate "frac" operation.

Figure 2:
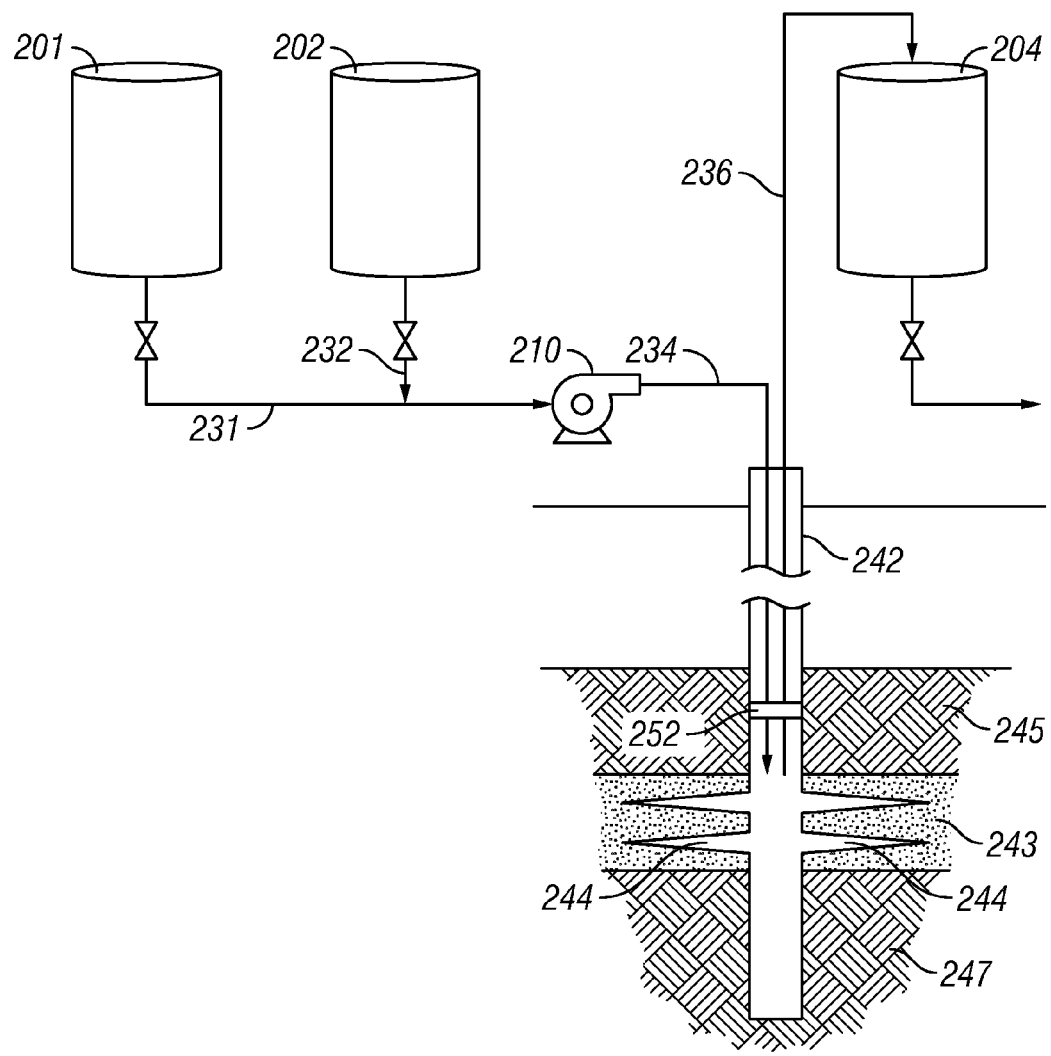
FIG. 2 is a diagrammatic representation of an embodiment of the process of the invention.

When the surface production equipment is installed the injected water is allowed to return ("flow back" or "produced water") to the surface for disposal, 114, shown in FIG. 2 and stored in tank 114 or pumped by pump 117 into disposal well 118. In hydrofracturing operations generally about 20-40% of the injected water remains in the formation. The "flow back" or "produced" water contains oil, salts, contaminants, and increased bacterial concentrations and, while generally problematic for recycling it is often necessary to recycle. It is increasingly required by Regulatory Agencies that the produced water be treated and reused. Disposal of untreated produced water is becoming increasingly restricted. In the Marcellus Shale and other regions virtually all the flow back water must be treated. In a study of biocides in several Barnett Shale wells the bacteria level increased at least one order of magnitude from the source water to produced water, e.g. from $1\times10^6$ bacteria/ml to $1\times10^7$ bacteria/ml.

Importantly, the multiplicity of SRP makes it difficult to predict those that will thrive and, therefore, be problematic (sulfide producing) under the conditions prevailing in the wellbore and in the reservoir formation. The conditions of salinity, nutrient content, water source, temperature, pressure and the like dictate which strains of prokaryotes will survive and reproduce.

This invention customizes the prokaryotes lysing organisms virulent for the problematic prokaryotes by producing those organisms in the wellbore under conditions that exist in the well and in the geologic formation. This greatly improves the likelihood that problematic bacteria will be abated or destroyed.

Thus, this invention provides for down-hole, in-situ production and proliferation of virulent lysing organisms at the site where the sulfate reducing prokaryotes (SRP) are most problematic. Producing virulent lysing organisms at the conditions and in the environment where they are causing harm provides most efficacious control. This is accomplished by providing both a concentrated solution of prokaryote lysing organisms together with a concentrated solution of host prokaryotes in the wellbore, preferably before and after hydrofracing ("fracing") to force virulent phage into fractured cracks of a hydro-fractured ("fraced") formation.

In contrast to other biocides, in which concentrations are typically measured as dissolved weight per unit volume (e.g., ppm), bacteriophage concentrations are measured as the number of organisms (or plaque-forming units, PFU) per unit volume. Phage concentrations for biocidal use are expected to range from 1,000 to $1\times10^{10}$ organisms/ml. Because the phage infection cycle begins with a period of random, diffusion-driven search followed by adsorption of the phage to the cell surface, the rate at which a phage can collide with and adsorb to its host is critical for its biocidal action. There are many factors that influence the rate phage adsorption, including, but not limited to, temperature, pressure, and the medium in which they reside. A critical factor governing the rate of phage adsorption (and subsequent proliferation) is the concentration of host cells and phage in the system. This is illustrated by reference to phage proliferation.

"The rate at which phages adsorb to their host is determined by second-order kinetics, as described by the relationship $-dp/dt=kPB$, where k is the phage adsorption rate constant in ml/min, P is the phage concentration, and B is the bacterial concentration. Although this process can be expressed in terms of second-order kinetics, under most conditions the behavior is pseudo-first order: during the adsorption process free phage are eliminated from the system by adsorption to a host bacterium, but the bacterium remains free in the system to adsorb additional phage. This relationship can also be expressed explicitly (here in terms of the rate constant k) as:

$$k = \frac{\ln(P_0/P_t)}{B \times t}$$

where $P_0$ is the initial concentration of free phage and $P_t$ is the concentration of free phage at time t. One conclusion which can be drawn from this expression is that the concentration of susceptible bacteria, B, and the adsorption rate constant, k, will strongly influence the rate at which free phage are able to locate and adsorb to their hosts. A second conclusion is that given constant parameters, the amount of phage adsorbed by bacteria in time period t is a constant proportion of the initial phage population. Thus, if 50% of the free phage in a given system are adsorbed during time t, the absolute number of phage adsorbed would be 50 if $P_0=100$ PFU, and 50,000 if $P_0$ were 100,000 PFU." (*Practical and theoretical considerations for the use of bacteriophages in the food systems*, Jason J Gill, in *Bacteriophages in the control of food and waterborne pathogens*, Parviz M Sabour and Mansel W Griffiths ed., June 2010, American Society for Microbiology Press, Washing D.C.)

These theoretical calculations based on the mathematical models serve as the guidelines for determining the amount of prokaryote lysing organisms and the time required to treat a given system under ideal conditions. For example, Table 1 shows the time (in minutes) required to adsorb a given percentage of phage (for example, 50%, 90%, and 99%) as a function of the target cell concentration (in CFU/ml), assuming k=5e-8 ml/min (a fast binding rate). Note this proportion is independent of the actual number of phage, so 50% of 100 PFU/ml means 50 PFU/ml bound, and 50% of 1,000,000 PFU/ml means 500,000 PFU/ml bound.

TABLE 1

The time (min) required to adsorb a given percentage of phage (in minutes) as a function of the target cell concentration (CFU/ml), assuming k = 5e−8 ml/min (a fast binding rate).

| Bacteria concentration | Time, Minutes - % Phage absorbed | | |
|---|---|---|---|
| CFU/ml | 50% | 90% | 99% |
| $1 \times 10^5$ | 138.6 | 460.5 | 921.0 |
| $5 \times 10^5$ | 27.7 | 92.1 | 184.2 |
| $1 \times 10^6$ | 13.9 | 46.1 | 92.1 |
| $5 \times 10^6$ | 2.8 | 9.2 | 8.2 |
| $1 \times 10^7$ | 1.4 | 4.6 | 1.8 |
| $5 \times 10^7$ | 0.3 | 0.9 | 0.9 |
| $1 \times 10^8$ | 0.0 | 0.5 | 0.2 |
| $5 \times 10^8$ | 0.0 | 0.1 | 0.2 |

Based on the above theoretical calculations, it can be estimated that for effective and timely prokaryote infection and lyse of host or target prokaryotes, it is necessary to have some idea about the concentration of prokaryotes that need to be treated down the well, and the amount of reduction that is required. In one model of treatment, target cell concentration is less relevant as long as enough lysing organisms can be introduced into the system to adsorb greater than 90% the cells in a timely manner, that is, a large excess of lysing organisms can be introduced into the system. Because of the very large volumes of fluid involved in this process, the introduction of enough lysing organisms to initially overwhelm the resident SRP population may not be feasible in some cases. On the other hand, the introduction of a smaller number of lysing organisms will rely on the timely amplification of prokaryote lysing organisms (net gain of progeny after lysis), in which case a relatively high concentration of potential hosts (greater than $10^6$-$10^7$ CFU/ml) are required. Thus, for practical application virulent lysing organism and target prokaryote concentrations will need to be above $10^6$ particles/ml to achieve meaningful replication of lysing organisms and destruction of prokaryotes, assuming a medium to high rate constant k. Such concentration will be conducive to effective and timely destruction of prokaryotes and replication of lysing organisms.

The present invention provides a means to achieve the necessary concentrations of lysing organisms through in-situ proliferation at the location where control of problematic prokaryoytes is most effective (in the well bore at the fractured formations).

FIG. 2 is a schematic representation of one embodiment of the invention. This representation is described in terms of bacteria and bacteriophage but applies as well to archaea and archaeal virus and to mixtures of bacteria, bacteriophage, archaea and archaeal viruses. Bacteriophage are injected into fractures (244 in FIG. 2) in a geologic formation in an oil or gas well together with a combination of host bacteria-sulfate reducing bacteria (SRB).

The SRB injected into the well function as hosts for effective lysing organism in-situ amplification down the well, so that the indigenous SRB and introduced bacteria will be lysed.

Referring to FIG. 2, flow-back or "produced" water is removed from the well, 242, through conduit 236 into vessel 204 for further separation and use. The "produced" water is partially cleaned by settling and/or filtering through a coarse filter to remove particle substantially larger than target bacteria. Target prokaryotes will, to an extent, be naturally selected by the conditions and environment. Therefore, it is preferred that they and their matching virulent lysing organism be those that exist down-hole in the well and formations. Typically the host SRP for in-situ lysing organism amplification are introduced into the well in the water used to hydrofracture the formation. Therefore, it is preferred to obtain prokaryotes from the well (or similar wells in the geographic area) for use in the invention.

When the well is ready for treating a solution of virulent lysing organisms for target SRB from vessel 201 (FIG. 2) is mixed with host SRB solution from vessel 202 at a concentration conducive to rapid adsorption of the phage to their hosts, such that most of the phage will be adsorbed to a host before passage by conduit 231 and 232 through pumps 210 (such as the frac pumps 106-109 shown in FIG. 1) by conduit 234 into the well so that the phage-infected cells and remaining phage will be forced into the fractures 244 in the formation 242 when the well is fractured. Packer 252 holds pressure on the well for fracturing. Since SRB are anaerobic it is important that the vessel 202 be blanketed with a non-oxygen gas—such as nitrogen, carbon dioxide or natural gas. Since vessel 201 contains only the lysing organisms that are not affected by oxygen, there is generally no need to control oxygen in vessel 201. It may be blanketed to prevent oxygen intruding into the anaerobic vessels. The SRB and lysing organism solutions may, alternatively, be pumped separately into the wellbore. Formations 245 and 247 are not to scale and are illustrative only, as is the shale formation 243 that is fractured by the high pressure "frac" water injection. Phage and host bacteria are forced into the fractures to allow the phage to replicate and reduce formation of additional SRB.

In another embodiment the SRP solution in vessel 202 and lysing organism solution from vessel 201 may be mixed with the initial "frac" water before injection for hydrofracing. It is beneficial if the host SRP and lysing organism solution be pumped in before hydrofracing and that it remain in the well bore for a sufficient time to allow proliferation of the lysing organisms by lysing target SRP in the well. Once proliferation is initiated more SRP (at appropriate concentrations) may be added to provide additional host for lysing organism proliferation. The object is to provide as high a concentration of lysing organisms as possible.

It is an advantage of one embodiment of this invention that the SRP isolated and concentrated from produced water in the well (or a nearby well, preferably in the same formation) will best represent the environment in the wellbore where problematic SRP will thrive and lysing organisms will proliferate. Using SRP from the well—like recycling the water—introduces no new microorganisms into the well that were not already there.

It is useful that the lysing organism solution injected at this stage be a classic "squeeze" (as that term is used in the industry) where the water pressure is sufficient to force the phage solution into existing fractures but below that pressure needed to further fracture the formation.

An effective amount of lysing organism and target SRP is that amount sufficient to result in a measurable reduction in sulfide production in the well over a period of several days.

In one embodiment SRP and virulent lysing organisms will be pumped into a well as the first hydrofracing water into each segment (if the fracturing is segmented). Subsequent "frac" water injection will then place the lysing organisms into fractures most remote from the well bore where customary biocides are unlikely to reach or to be effective. By mixing the lysing organism with host SRP a kind of in-situ bioreactor is provided so that when additional water is added to the well concentrations remain sufficiently high to continue lysing SRP and continue producing progeny lysing organisms. This mechanism is effective in "water floods" where water is passed from the "flood" well to a "recovery" well.

Figure 3:
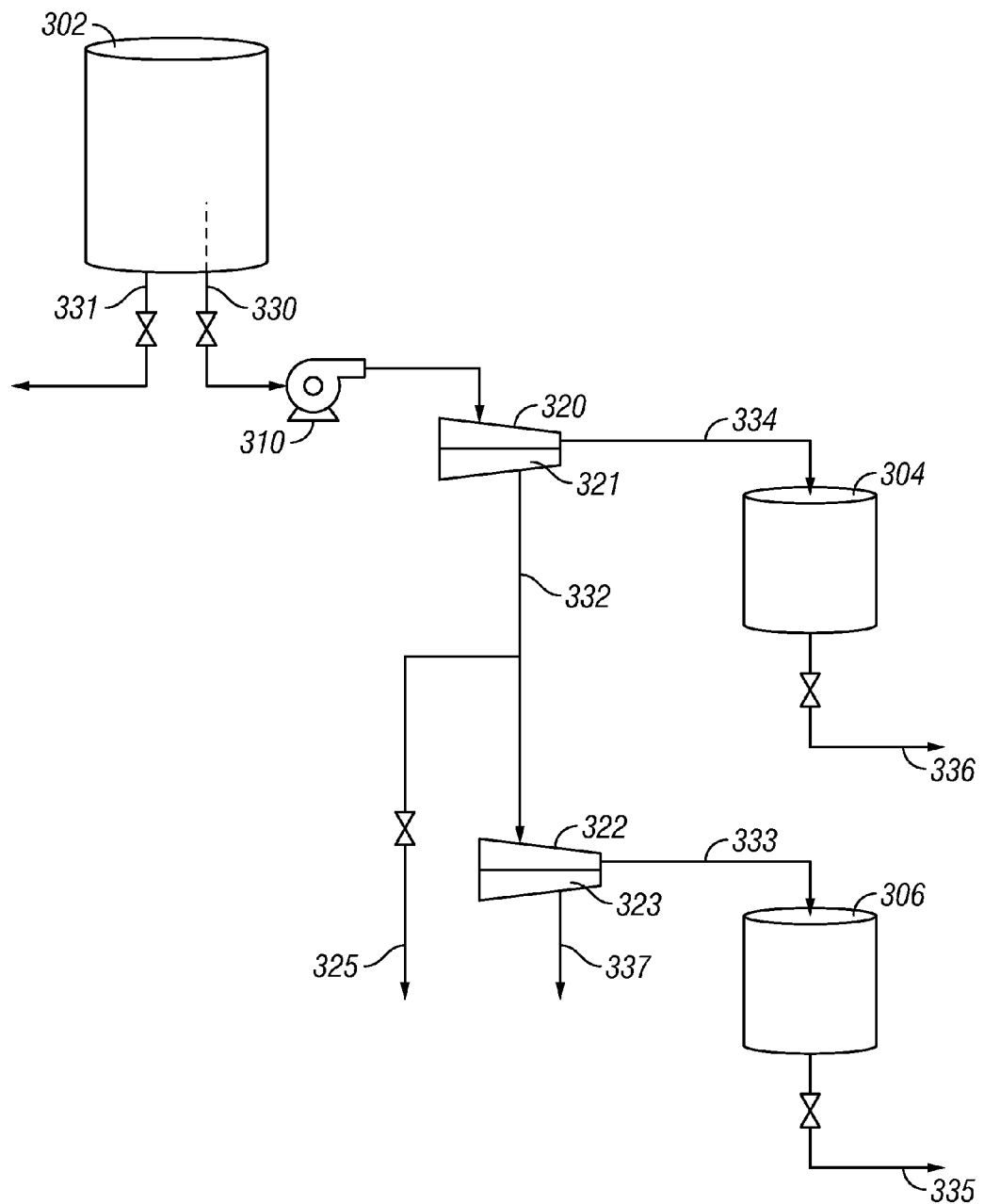
FIG. 3 is diagrammatic representation of the bacteria and phage concentration of an aspect of the process of the invention.

In another aspect of the invention a method of obtaining and producing host SRP and virulent lysing organisms is illustrated by reference to FIG. 3. "Produced" water is collected from a target well or another well in the geographic area (for example, as in vessel 204 in FIG. 2). This water is transferred to vessel 302 (FIG. 3), prescreened and pumped to the separation means 320 (here a tangential flow filtration filter) where target SRP cells are retained upstream of the filter and water with smaller particles, including the phages endogenous to the water sample, pass out through conduit 332 to a second separation means 322 (here a tangential flow filtration filter) where the smaller particles, including phages, are retained and the clear water is passed out through conduit 337.

This operation may be conducted at a central site where analytical, culturing and other production aids are located. The separation filter 321 screen will generally be about 0.2 μm and the screen of the second filter 322 will have the molecular weight cutoffs (MWCO) at about 100-300 kDa. Thus, target SRP (together with other similar sized microorganisms) will be concentrated in filter 321 and phage in filter 322. Filtration mesh size in the range of 0.45-0.2 μm is suitable to capture most SRP. Filter mesh size 0.1-0.02 μm is suitable to concentrate most prokaryote lysing organisms (bacteriophage and/or archaeal viruses).

The separated SRP solution passes by conduit 334 to vessel 304 for storage and use. Separated lysing organism solution passes by conduit 333 to vessel 306 for storage and use. It is desired that the SRP concentration and the lysing organism concentration be as high as possible—at least $1 \times 10^6$ to $1 \times 10^{12}$ particles/ml. Concentrations above $1 \times 10^8$ are preferred.

It is expected that lysing organisms for all the host and target SRP will coexist in the indigenous water so that both can be concentrated from portions of the "produced water." However, if not, lysing organisms may be supplemented by lysing organisms from other sources, as for example, by isolation from surface water or mud sources in the area of the well or from a collection already available.

Additional SRP may be produced and the concentration of SRP solutions enhanced by additional culturing in a medium consistent with the source water.

Another embodiment is compositions of SRP produced by filtration of "produced water" as described above to provide a composition comprising a mixture of prokaryotes recovered from oil or gas well produced water and concentrated to a concentration of at least $1 \times 10^6$ particles/ml. This composition will preferably be that recovered by filtration with a mesh size filter in the range of 0.45-0.2 μm.

The invention is additionally a composition of prokaryote lysing organisms recovered from oil or gas well produced water and concentrated to a concentration of at least $1 \times 10^6$ particles/ml. This composition will preferably be that recovered by filtration with a mesh size filter in the range of 0.1-0.02 μm.

Location of and commercial production of commercial scale phage virulent for SRB can be accomplished by means described in prior art references such as published applications US 2009/0180992, published 7/16,2009, US 2010/9243563 published Sep. 30, 2010, WO/2009/076642 and K. Kamimura and M. Araki: Isolation and Characterization of a Bacteriophage Lytic for *Desulfovrio salexigens*, a Salt-Requiring. Sulfate-Reducing Bacterium, Applied and Environmental Microbiology, March 1989 p. 645-648, Vo. 55, No. 3, the relevant disclosures of which are incorporated herein by reference. Other SRP, including archaea may be similarly located, isolated and produced.

In this specification, the invention has been described with reference to specific embodiments. It will, however, be evident that various modifications and changes can be made thereto without departing from the broader spirit and scope of the invention as set forth in the appended claims. The specification is, accordingly, to be regarded in an illustrative rather than a restrictive sense. Therefore, the scope of the invention should be limited only by the appended claims.

The invention claimed is:

1. A method of preparing an oil and gas geological formation for hydrofracturing or water flood by introducing before hydrofracturing or water flood operations a combination of sulfate-reducing prokaryotes (SRP) and lysing organisms virulent for said sulfate-reducing prokaryotes (SRP) in sufficient amount and concentration to cause the bacteriophage to replicate by lysing said sulfate-reducing prokaryotes (SRP).

2. The method of claim 1 wherein the sulfate-reducing prokaryotes comprise sulfate-reducing bacteria and sulfate-reducing Archaea.

3. The method of claim 1 wherein a mixture of sulfate prokaryotes and matching virulent lysing organisms are introduced into a well bore before hyrofracturing water is pumped in.

4. The method of claim 1 wherein the sulfate-reducing prokaryotes are recovered from water produced from the wellbore or from a similar wellbore.

5. The method of claim 4 wherein the prokaryotes and lysing organisms are recovered by sequential tangential flow filtration.

6. The method of claim 5 wherein the prokaryotes are first recovered from the water followed by recovery of the virulent lysing organisms.

7. The method of claim 1 wherein the prokaryotes are bacteria and the lysing organism are bacteriophage.

8. The method of claim 1 wherein the prokaryotes are archaea and the lysing organism are archaeal viruses.

9. The method of claim 1 wherein the sulfate-reducing prokaryotes are recovered from water produced from the wellbore or from a similar wellbore and multiplied by culturing before reintroduction into the wellbore.

10. The method of claim 1 wherein the prokaryotes and lysing organisms are introduced into the wellbore in aqueous solution concentrations of at least $1 \times 10^6$ particles per ml.

11. A method of remediating sulfate-reducing prokaryotes (SRP) in oil and gas geological formations comprising introducing into a wellbore in a formation during drilling operations a combination of sulfate-reducing prokaryotes (SRP) and lysing organisms virulent for said sulfate-reducing prokaryotes (SRP) in sufficient amount and concentration to cause the bacteriophage to replicate by lysing said sulfate-reducing prokaryotes (SRP).

12. The method of claim 11 wherein the sulfate-reducing prokaryotes are recovered from water produced from the wellbore or from a similar wellbore.

\* \* \* \* \*